(12) United States Patent
Zobele

(10) Patent No.: US 7,140,553 B2
(45) Date of Patent: Nov. 28, 2006

(54) DEVICE FOR DIFFUSING VOLATILE SUBSTANCES, IN PARTICULAR DEODORANTS FOR VEHICLE INTERIORS

(75) Inventor: Franco Zobele, Trento (IT)

(73) Assignee: Zobele Holding SpA, Trento (IT)

( * ) Notice: Subject to any disclaimer, the term of this patent is extended or adjusted under 35 U.S.C. 154(b) by 192 days.

(21) Appl. No.: 10/863,941

(22) Filed: Jun. 9, 2004

(65) Prior Publication Data
US 2005/0001053 A1    Jan. 6, 2005

(30) Foreign Application Priority Data
Jun. 10, 2003   (IT)   ................. MI2003A001165

(51) Int. Cl.
*A24F 25/00* (2006.01)
(52) U.S. Cl. ............. 239/34; 239/44; 239/47; 239/50; 239/51.5; 239/58; 239/59
(58) Field of Classification Search .......... 239/36, 239/44, 47, 50, 51.5, 58, 59
See application file for complete search history.

(56) References Cited

U.S. PATENT DOCUMENTS

| | | | | |
|---|---|---|---|---|
| 4,258,874 A | * | 3/1981 | Webinger et al. | 229/120 |
| 4,402,433 A | * | 9/1983 | Webinger | 222/485 |
| 4,621,768 A | * | 11/1986 | Lhoste et al. | 239/44 |
| 4,630,775 A | * | 12/1986 | Mandon et al. | 239/56 |
| 4,739,928 A | * | 4/1988 | O'Neil | 239/45 |
| 6,514,467 B1 | * | 2/2003 | Bulsink et al. | 422/122 |
| 7,007,863 B1 | * | 3/2006 | Kotary et al. | 239/44 |

FOREIGN PATENT DOCUMENTS

| | | |
|---|---|---|
| DE | 44 33 954 A1 | 3/1996 |
| EP | 1 031 446 A1 | 8/2000 |
| GB | 2 181 649 A | 4/1987 |

* cited by examiner

*Primary Examiner*—David A. Scherbel
*Assistant Examiner*—Trevor McGraw
(74) *Attorney, Agent, or Firm*—Merchant & Gould

(57) ABSTRACT

A device for diffusing volatile substances, particularly deodorants for vehicle interiors. The device comprises a container designed to contain a liquid volatile substance to be diffused, a wick disposed partially in the container and a lid applied to the container around one end of the wick. The lid comprises a cap provided with slots and mounted revolving with respect to the axis of the wick. Between the cap and the wick there is interposed an intermediate element integral with the lid. The intermediate element has a U-bolt structure and is provided with slots.

12 Claims, 3 Drawing Sheets

DEVICE FOR DIFFUSING VOLATILE SUBSTANCES, IN PARTICULAR DEODORANTS FOR VEHICLE INTERIORS

The present invention refers to a diffuser device for diffusing volatile substances, particularly deodorants for vehicle interiors.

There are currently available on the market various types of diffuser devices for deodorant substances, which are generally applied to an air vent inside the vehicle interior, to perfume the inside of the passenger and driver compartment.

A known diffuser device of this type comprises:
- a container or bottle inside which is contained the volatile substance in which the active principles to be diffused are dissolved,
- a wick disposed at least partially in said container so as to be impregnated with said volatile substance, and
- a diffusing lid, provided with slots, applied to the container around the wick so as to generate air passages to allow diffusion toward the outside of the deodorant with which the wick is impregnated.

A cap is mounted axially movable in the lid to adjust opening of the air passages and thus the quantity of volatile substances to be diffused. Said cap is moved axially by rotation of a ring which carries a gear meshing with a rack integral with the cap.

Such a diffuser device, however, has a somewhat complex structure, due to the gear-rack coupling which serves for movement of the cap.

An object of the present invention is to eliminate the drawbacks of the prior art, providing a diffuser device which is inexpensive and simple to produce.

Another object of the present invention is to provide a diffuser device that is practical for the user and able to allow efficient adjustment of the amount of volatile substances to be diffused.

These objects are achieved in accordance with the invention with the characteristics disclosed herein.

Advantageous embodiments of the invention are apparent from the dependent claims.

The diffuser device according to the invention comprises:
- a container able to contain a liquid volatile substance to be diffused,
- a wick disposed partially in the container, and
- a lid applied to the container around one end of the wick.

According to the invention, a cap with slots is provided in the lid, mounted revolving with respect to the axis of the wick. An intermediate element is interposed between the cap and the wick. The intermediate element has an U-bolt structure and is provided with slits.

Therefore, by rotating the cap with respect to the intermediate U-bolt structure, it is possible to regulate the airflow through the slits of the intermediate element and of the revolving cap.

Such a solution proves structurally simple and ensures various possibilities of regulating the airflow from the wick to the outside of the lid.

Further characteristics of the invention will be made clearer by the detailed description that follows, referring to a purely exemplary and therefore non limiting embodiment thereof, illustrated in the appended drawings, in which.

Figure 1:
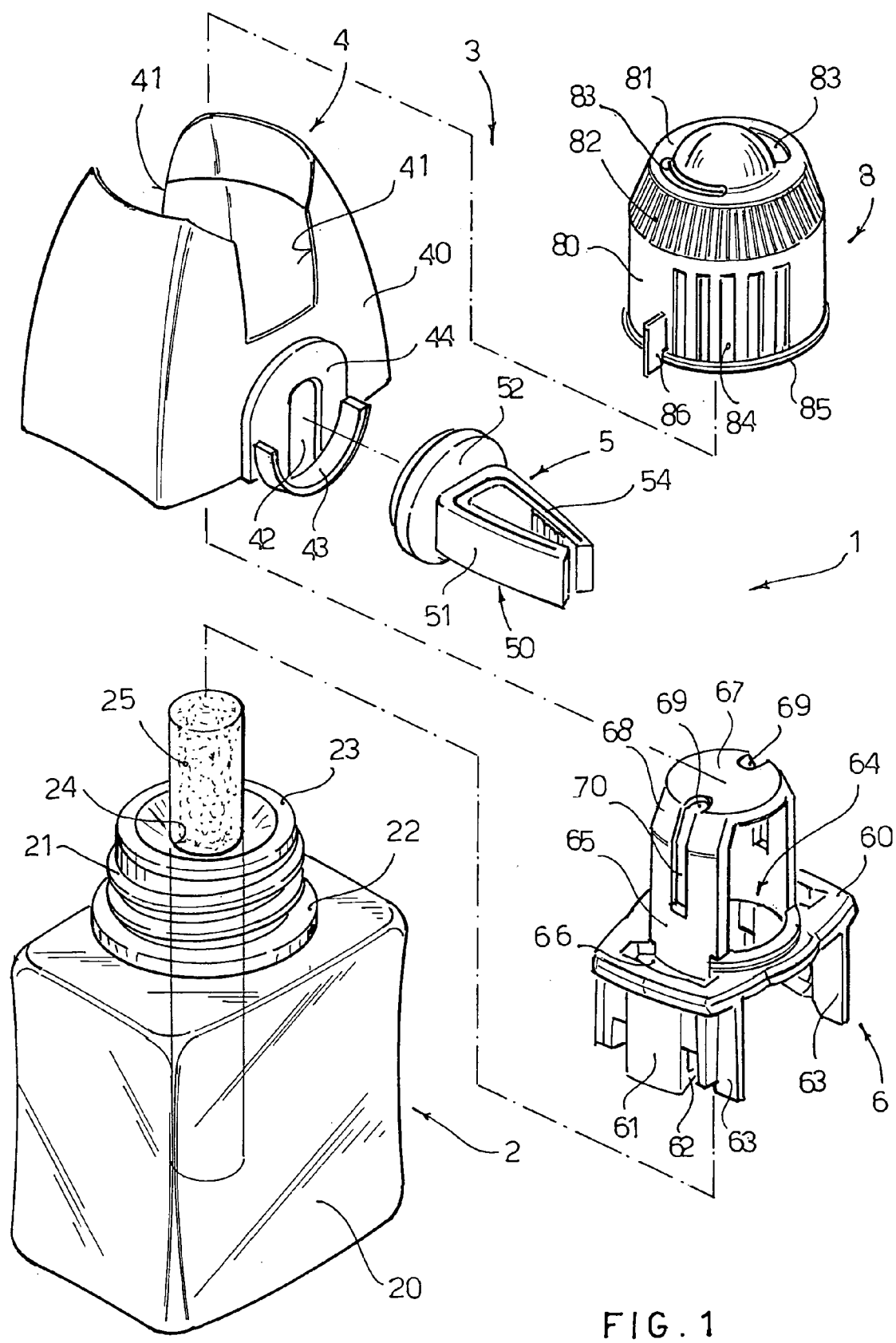
FIG. 1 is a perspective exploded view illustrating the diffuser device according to the invention.

The diffuser device according to the invention, denoted as a whole with reference numeral 1, is described with the aid of the figures.

With reference to FIG. 1, the diffuser device 1 comprises a container 2 and a lid 3 which can be applied to the container 2. The container 2 consists of a bottle 20 designed to contain a solution in which the active principles to be diffused are dissolved. The bottle 20 has a threaded neck 21 on which an annular abutment flange 22 protruding radially outward is formed. A funnel shaped flange 23 which has a through hole 24 through with a substantially cylindrical shaped wick 25 passes is disposed in the mouth of the neck 21.

The wick 25 can be made of any absorbent material able to absorb and to retain the solution contained in the bottle 20. The bottom part of the wick 25 is disposed axially inside the bottle 20, whilst the top part thereof is situated outside the bottle 20.

The lid 3 consists of an outer shell 4, a coupling device 5, an intermediate element 6 and a cap 8.

The outer shell 4 has a substantially truncated pyramid-shaped body 40 with a rectangular base, hollow on the inside and open at the bottom and at the top. Two rectangular slots 41 open at the top and disposed in opposite positions are formed respectively in the two greater side walls of the body 40.

In one of the two greater side walls of the body 40, beneath a slot 41 there is formed a through hole 42, delimited at the bottom by a flange 43 with a curved profile. An upturned U-shaped protruding portion 44 is provided around the hole 42 on the wall of the body 40.

The coupling device 5 is in the form of a clip 50 consisting of a small flexible bar 51 bent into a U shape so as to form two gripping jaws. A metal core 54 can be provided inside the bar 51 to improve flexibility. The clip 50 can be hooked onto any protruding element of the interior of a vehicle, such as, for example, the grille of an air vent.

The clip 50 is connected to a disc-shaped flange 52 behind which a pawl (not shown) which engages revolvingly inside the hole 42 of the outer shell is provided. In this manner the flange 52 of the clip abuts against a protruding portion 44 of the outer shell and the clip 50 can turn around the axis of the hole 42 in the outer shell, to allow correct positioning of the diffuser.

The intermediate element 6 comprises a transverse plate 60, with a substantially rectangular shape, designed to be disposed in an intermediate position inside the outer shell 4.

Figure 2:
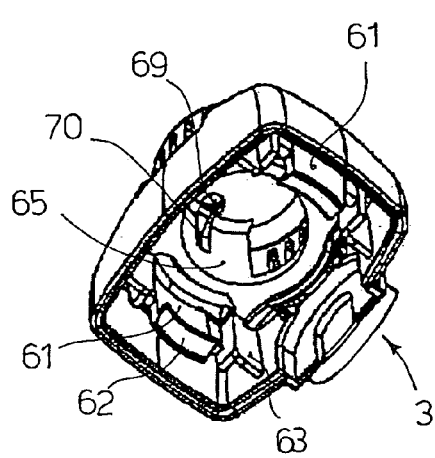
FIG. 2 is a perspective bottom view illustrating the inside of the lid of the diffuser device according to the invention.

Connected to the transverse plate 60 there are two flexible tongues 61 which longitudinally protrude downward near the respective lower side edges of the transverse plate 60. As shown in FIG. 2, each flexible tongue 61 has at its end a tooth 62 which protrudes inward.

The distance between the teeth 62 of the two opposite tongues 61 is chosen so that the teeth 62 can engage in the annular flange 22 of the neck of the bottle, retaining the lid 3 on the bottle 2.

Four longitudinally downward protruding feet 63 are provided near the four corners of the transverse plate 60.

A circular through hole 64 designed to allow the wick 25 to pass is formed in the transverse plate 60, in a central position. Two longitudinal partitions 65 disposed in diametrically opposite positions near the circumferential edge which delimits the hole 64 are provided on the transverse plate 60.

Two slotted through holes 66 are formed in the plate 60, between the partitions 65 and the lower side edges of the plate 60.

The partitions 65 support at the top an upper disc-shaped part 67 disposed on a horizontal plane parallel to the transverse plate 60. A tapered connecting portion 68 with an upwardly decreasing diameter is provided between the side partitions 65 and the upper disc-shaped part 67. So, the two lateral partitions 65 and the upper part 67 form a U-bolt structure.

Two through holes 69, disposed in diametrically opposite positions near the periphery of the disc-shaped part 67 and near the connecting portions 68, are formed in the upper disc-shaped part 67. Each hole 69 is connected to a respective side opening 70 obtained like a through slot in the connecting part 68 and in the side partition 65.

The intermediate element 6, as described, can be obtained in a single piece by injection moulding of plastic material and then it is fixed inside the outer shell 4 by welding or by gluing or by clamping. It is clear that the intermediate element 6 can also be made in a single piece with the outer shell 4.

A cap 8 is fitted on the intermediate element 60. The cap 8 consists of a substantially cylindrical body 80 hollow on the inside and open at the bottom. At the top, the body 80 has a substantially disc-shaped top wall 81 connected to the cylindrical body 80 by a truncated conical transitional portion 82.

Two through openings 83, having a substantially curved shape and disposed in diametrically opposite positions, are formed peripherally in the top wall 81.

In the side wall of the body 80 there is formed a first plurality of longitudinal through slots 84 (five slots in the example) so as to form a first grid and a second plurality of longitudinal through slots so as to form a second grid. The first grid of slots 84 is disposed in a diametrically opposite position with respect to the second grid of slots 84 and each grid extends over an arc subtended by an angle at the centre of about 90°.

In this manner, in the side wall of the body 80 there are provided two grids of slots 84 separated from each other, respectively, by two solid portions of side wall which extend on an arc subtended by an angle at the centre of 90°.

The body 80 has in its lower edge an abutment flange 85 which protrudes radially outward. A stop pin 86 extends radially outward from the annular abutment flange 85. Once the intermediate element 6 is situated inside the outer shell 4, the cap 8 is mounted revolving on the U-bolt structure of the intermediate element 6 so as to surround the lateral partitions 65 of the intermediate element 6. The bottom edge of the annular flange 85 of the cap 8 abuts against the transverse plate 60 of the intermediate element, whilst the top edge of the annular flange 85 is retained by suitable protrusions (not shown) formed in the inner surface of the shell 4.

The rotation stroke of the cap 8 is limited to about 90°. In fact the stop pin 86 of the cap 8 is delimited between two protrusions of the inner surface of the shell 4 spaced apart from each other by an angle of about 90°.

Figure 3:
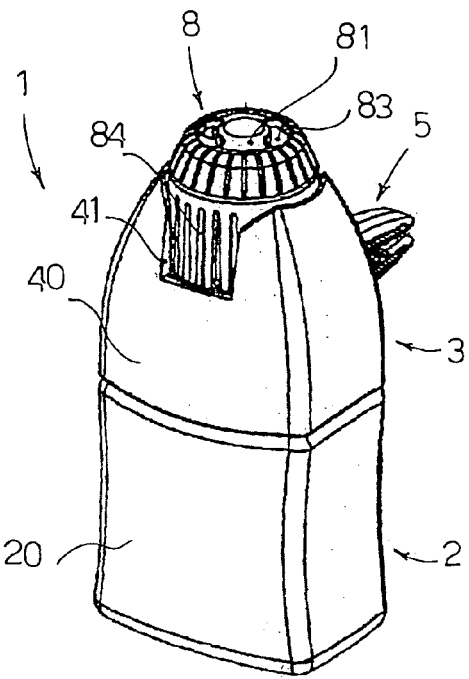
FIG. 3 is a perspective view illustrating the diffuser device of FIG. 1 assembled, in which the revolving cap is in the completely open position.
Figure 4:
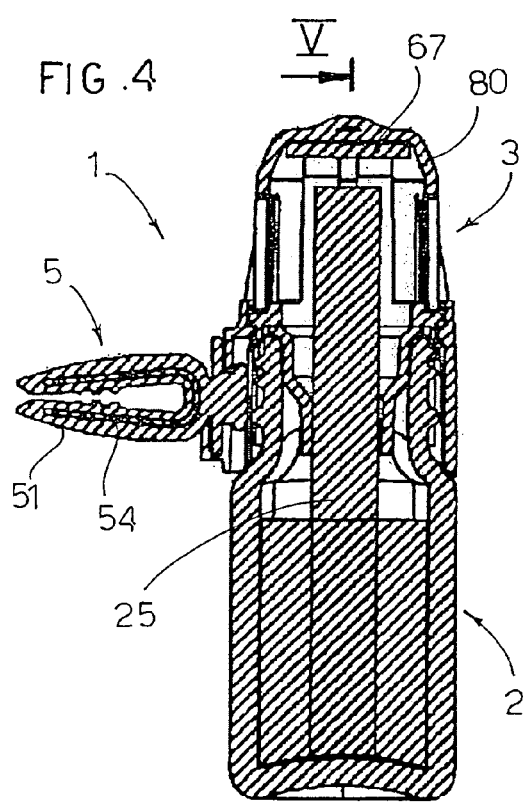
FIG. 4 is an axial sectional view of the diffuser device of FIG. 3.
Figure 5:
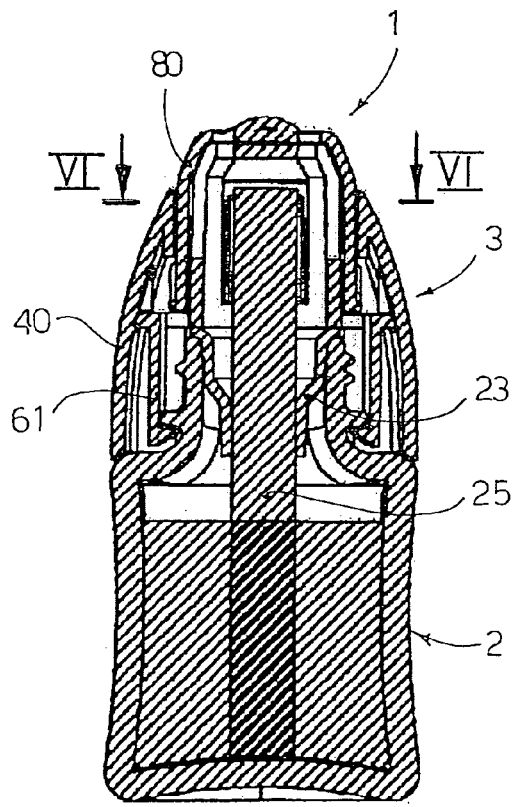
FIG. 5 is an axial sectional view along the section plane V—V of FIG. 4.

Once the lid 3 has been assembled, as shown in FIGS. 3–5, it is mounted on the container 2, so that the teeth 62 of the tongues 61 of the intermediate element engage with the annular flange 22 of the neck of the bottle. Thus the top part of the wick 25 passes through the central hole 64 of the transverse plate 60 of the intermediate element and is disposed between the two side partitions 65 of the intermediate element beneath the top wall 67 of the intermediate element.

Operation of the diffuser device 1 is described below.

Figure 6:
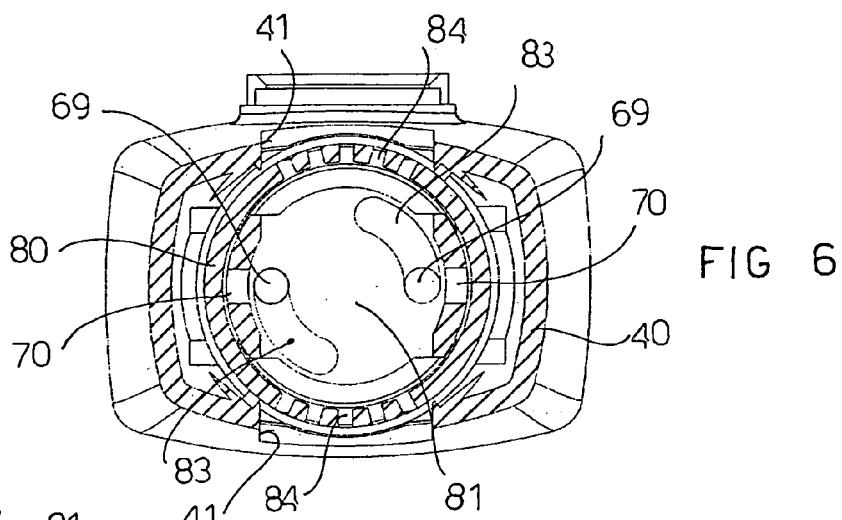
FIG. 6 is top plan view of the diffuser device of FIG. 3 in the open position, in which, for greater clarity, the lid has been sectioned along the transverse section plane VI—VI of FIG. 5.

FIGS. 3–5 illustrate the assembled diffuser device, in which the cap 8 is disposed in its completely open position. As shown in particular in FIGS. 3 and 6, when the cap 8 is in the completely open position, the first and second grid of slots 84 are completely uncovered, disposed perfectly in register with the two slots 41 of the outer shell 40.

Furthermore, the holes 69 of the top part 67 of the intermediate element are uncovered, near the end of the respective curved slots 83 of the top wall 81 of the cap.

In this situation the airflow from the inside of the lid 3 to the outside is maximum. In fact, there is a maximum radial airflow, in which the active principles diffused by the top part of the wick 25 pass through the gaps defined by the two side partitions 65 of the intermediate element, through the slots 84 of the cap and through the slots 41 of the outer shell and reach the outside of the lid 3 diffusing into the surrounding environment.

At the same time, in this situation there is a longitudinal airflow, in which the active principles pass from the top part of the wick 25 through the holes 69 in the top wall of the intermediate element, pass through the curved slots 83 of the top part of the cap and diffuse to the outside.

Figure 7:
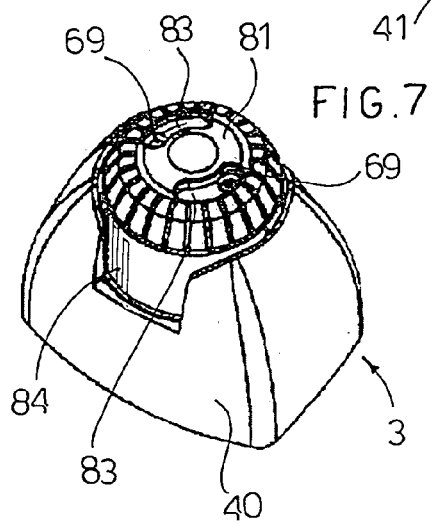
FIG. 7 is a perspective top view of the lid of the diffuser device, in which the revolving cap is illustrated in a half-open position.
Figure 7A:
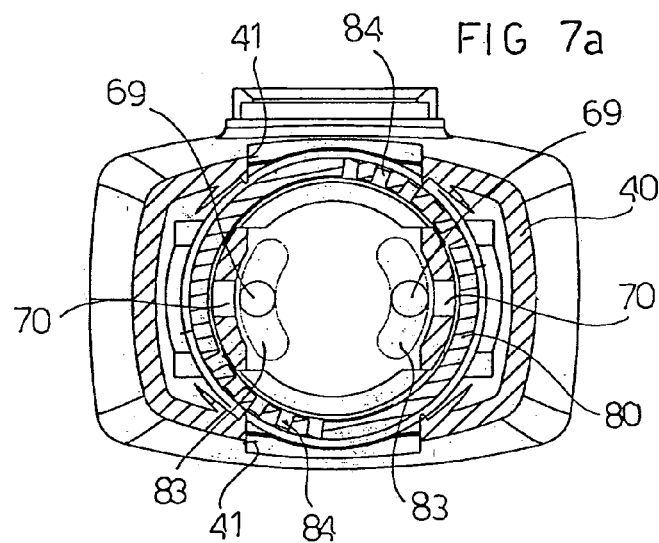
FIG. 7a is a view like FIG. 6, but illustrating the revolving cap in the half-open position.

As shown in FIGS. 7 and 7a, by turning the cap 8 by about 45° with respect to its completely open position, it is placed in its semi-open position in which the airflow from the inside to the outside of the lid 3 is medium. In this situation only a partial number of slots 84 of the first and of the second grid are uncovered by the slots 41 of the shell, the other slots 84 of the first and of the second grid being covered by the body 40 of the shell. Furthermore, in this situation the holes 69 of the top wall of the intermediate element are uncovered and disposed substantially in a central position of the curved slots 83 of the top wall of the cap.

As a result, in this situation there is a medium radial airflow, because some slots 84 of the grid remain covered by the outer shell, and a maximum longitudinal airflow, since the holes 69 of the intermediate element continue to remain uncovered.

Figure 8:
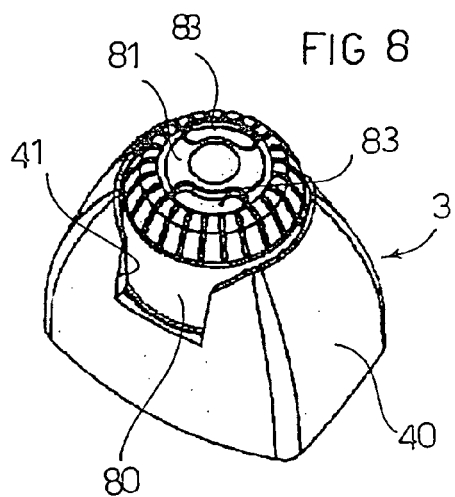
FIG. 8 is a view like FIG. 7, but illustrating the revolving cap in the closed position.
Figure 8A:
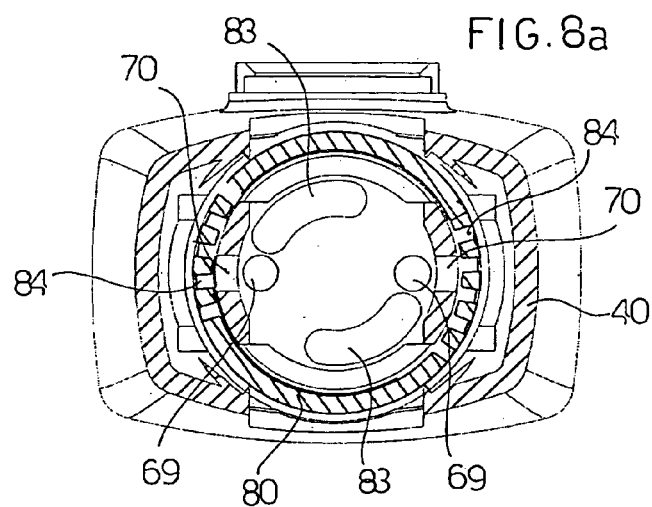
FIG. 8a is a view like FIG. 6, but illustrating the revolving cap in the closed position.

As shown in FIGS. 8e 8a, by turning the cap 8 by about 90° with respect to its completely open position, it is placed in its closed position in which the airflow from the inside to the outside of the lid 3 is minimum. In this situation all the slots 84 of the first and of the second grid of the cap 8 are covered by the shell 4, thus there is no radial airflow. Furthermore, in this situation the holes 69 of the top wall of the intermediate element are covered by the top wall 81 of the cap, thus there is no longitudinal upward airflow.

However, as can be noted clearly by FIG. 8a, in this situation the side channels 70 of the side partitions 65 of the intermediate element coincide with one or more slots 84 of the first and of the second grid of the cap.

As a result, in this situation there is a radial airflow which passes from the wick 25 through the side channels 70 of the intermediate element and through the slots 84 of the grids, then the airflow moves longitudinally downward through the slots 66 formed in the transverse plate 60 of the intermediated element 6 and is diffused inside the outer shell 4 beneath the transverse plate 60.

Finally, the airflow contained beneath the transverse plate 60 exits from the lower edge of the outer shell 4, given that there is no seal between the lower edge of the outer shell 4 and the body of the container 2. It is clear that in this situation the flow of air from the inside of the lid 3 towards the outside is minimal.

The invention claimed is:

1. A device for diffusing volatile substances, in particular deodorants for vehicle interiors, comprising:
    a container designed to contain a volatile liquid substance to be diffused,
    a wick disposed partially inside the container,
    a lid fitted on the container around one end of the wick, provided with a mobile element which can be moved to regulate the airflow from the wick to the outside of the lid, characterised in that:
    said mobile element comprises a cap, provided with slots and mounted for rotation with respect to the axis of the wick, between said cap and said wick being interposed an intermediate element having a U-shape structure and being provided with slots, said lid comprising an outer shell which partially covers said rotatable cap, and said outer shell having at least one slot able to leave uncovered at least some of said slots of the rotatable cap.

2. A diffuser device according to claim 1 characterised in that said rotatable cap has a substantially cylindrical shape and is hollow on the inside with longitudinal slots provided in its side wall.

3. A diffuser device according to claim 2, characterised in that said longitudinal slots are disposed in the side wall of the cap so as to form two grids disposed in diametrically opposite positions and in that said outer shell has two slots in diametrically opposite positions.

4. A diffuser device according to claim 1, characterised in that said rotatable cap comprises a top wall provided with at least one slot and in that said intermediate element has an upper part provided with at least one hole.

5. A device for diffusing volatile substances, in particular deodorants for vehicle interiors, comprising:
    a container designed to contain a volatile liquid substance to be diffused,
    a wick disposed partially inside the container,
    a lid fitted on the container around one end of the wick, provided with a mobile element which can be moved to regulate the airflow from the wick to the outside of the lid, characterised in that said mobile element comprises a cap, provided with slots and mounted for rotation with respect to the axis of the wick, between said cap and said wick being interposed an intermediate element having a U-shape structure and being provided with slots;
    said rotatable cap comprises a top wall provided with at least one slot and in that said intermediate element has an upper part provided with at least one hole; and
    in said top wall of the rotatable cap there are peripherally provided two curved slots disposed in diametrically opposite positions and in that in said upper part of the intermediate element there are provided two holes disposed in diametrically opposite positions.

6. A diffuser device according to claim 1, characterised in that said intermediate element comprises side walls provided with longitudinal slots.

7. A diffuser device according to claim 6, characterised in that said intermediate element comprises two side walls disposed in diametrically opposite positions, provided with respective longitudinal slots.

8. A device for diffusing volatile substances, in particular deodorants for vehicle interiors, comprising:
    a container designed to contain a volatile liquid substance to be diffused,
    a wick disposed partially inside the container,
    a lid fitted on the container around one end of the wick, provided with a mobile element which can be moved to regulate the airflow from the wick to the outside of the lid, characterised in that said mobile element comprises a cap, provided with slots and mounted for rotation with respect to the axis of the wick, between said cap and said wick being interposed an intermediate element having a U-shape structure and being provided with slots; and
    said intermediate element comprises a transverse plate supporting said U-shape structure and provided with a central hole for passage of the wick.

9. A diffuser device according to claim 8, characterised in that said transverse plate has two slots disposed externally with respect to said U-shape structure.

10. A diffuser device according to claim 8, characterised in that beneath said transverse plate of the intermediate element there are provided flexible tongues provided with teeth to couple to a flange of said container.

11. A device for diffusing volatile substances, in particular deodorants for vehicle interiors, comprising:
    a container designed to contain a volatile liquid substance to be diffused,
    a wick disposed partially inside the container,
    a lid fitted on the container around one end of the wick, provided with a mobile element which can be moved to regulate the airflow from the wick to the outside of the lid, characterised in that said mobile element comprises a cap, provided with slots and mounted for rotation with respect to the axis of the wick, between said cap and said wick being interposed an intermediate element having a U-shape structure and being provided with slots; and
    the diffuser device comprises a coupling means applied to said cap to couple the diffuser device to an external element.

12. A diffuser device according to claim 11, characterised in that said coupling means is a clip.

* * * * *